United States Patent [19]
Rahman et al.

[11] 3,993,754
[45] Nov. 23, 1976

[54] LIPOSOME-ENCAPSULATED ACTINOMYCIN FOR CANCER CHEMOTHERAPY

[75] Inventors: Yueh-Erh Rahman; Elizabeth A. Cerny, both of Downers Grove, Ill.

[73] Assignee: The United States of America as represented by the United States Energy Research and Development Administration, Washington, D.C.

[22] Filed: Oct. 9, 1974

[21] Appl. No.: 513,210

[52] U.S. Cl. .................................................. 424/177
[51] Int. Cl.$^2$.......................................... A61K 37/02
[58] Field of Search ..................................... 424/177

[56] References Cited
OTHER PUBLICATIONS
Drugs Used Against Cancer, NIH, Apr. 1972.

*Primary Examiner*—Jerome D. Goldberg
*Attorney, Agent, or Firm*—Dean E. Carlson; Arthur A. Churm; Robert J. Fisher

[57] ABSTRACT

An improved method is provided for chemotherapy of malignant tumors by injection of antitumor drugs. The antitumor drug is encapsulated within liposomes and the liposomes containing the encapsulated drug are injected into the body. The encapsulated drug penetrates into the tumor cells where the drug is slowly released and induces degeneration and death of the tumor cells, while any toxicity to the host body is reduced. Liposome encapsulation of actinomycin D has been found to be particularly effective in treating cancerous abdominal tumors, while drastically reducing the toxicity of actinomycin D to the host.

4 Claims, 2 Drawing Figures

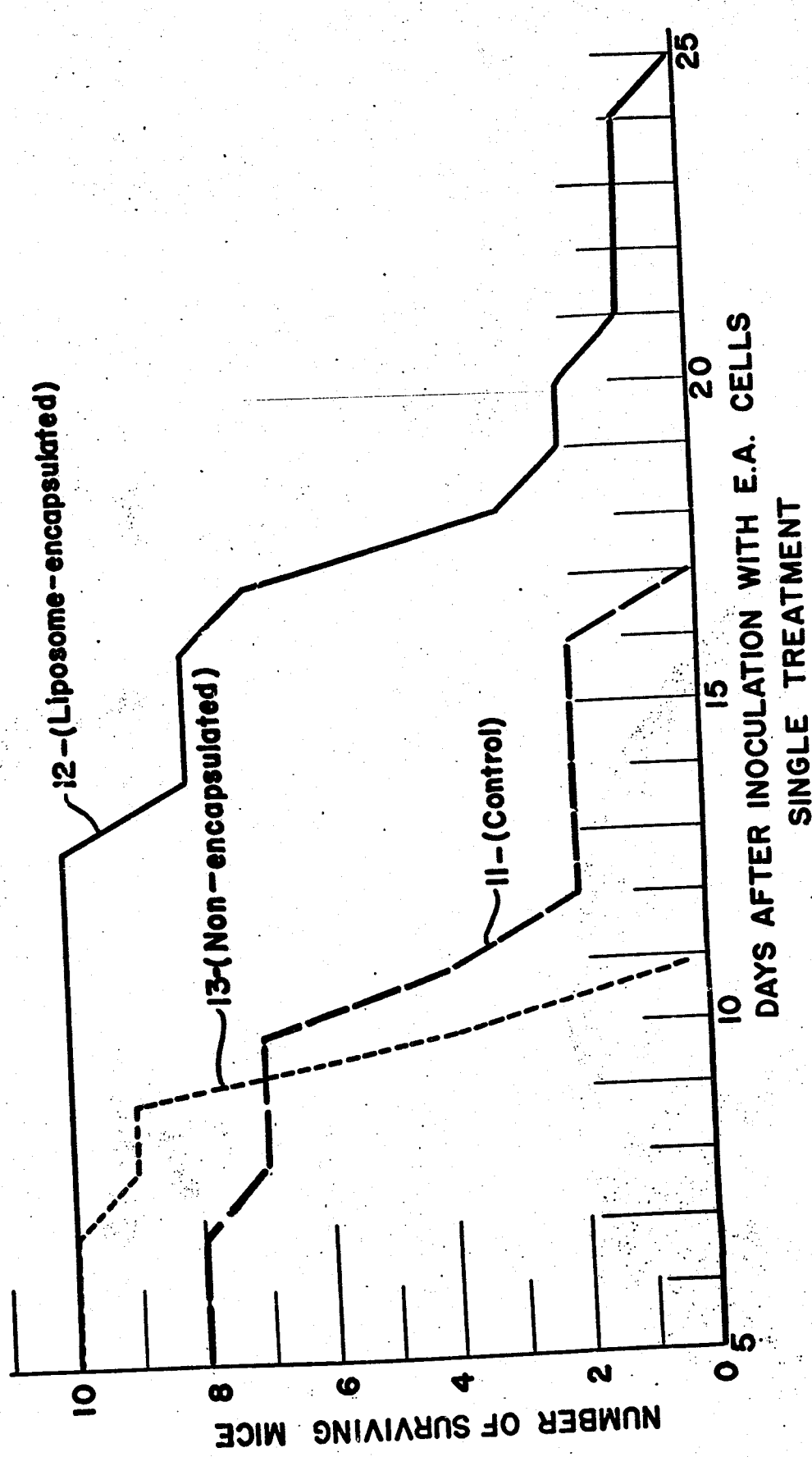

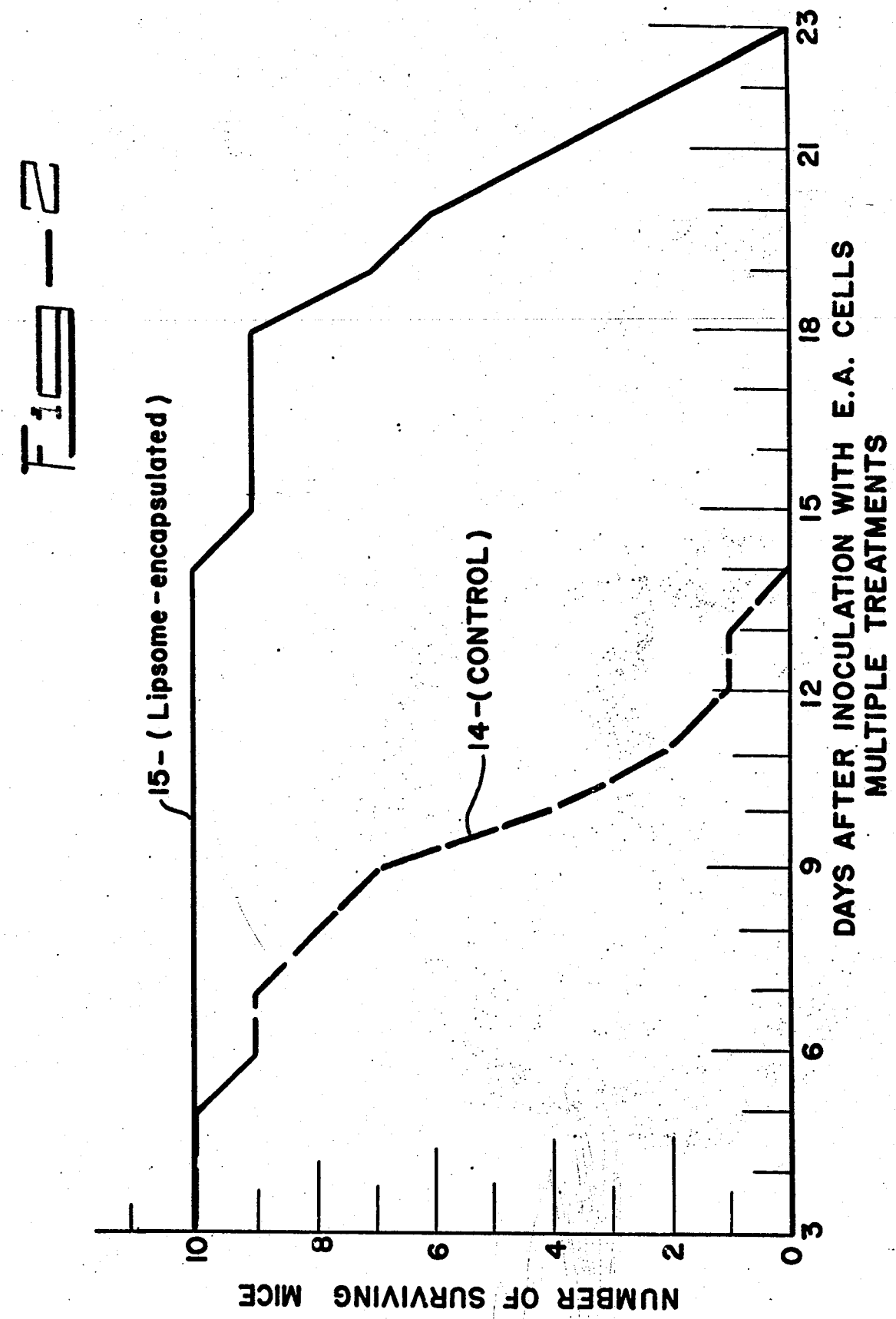

LIPOSOME-ENCAPSULATED ACTINOMYCIN FOR CANCER CHEMOTHERAPY

CONTRACTUAL ORIGIN OF THE INVENTION

The invention described herein was made in the course of, or under, a contract with the UNITED STATES ATOMIC ENERGY COMMISSION.

BACKGROUND OF THE INVENTION

While an actual cure for cancer has yet to be found, significant progress has been made in developing methods and techniques for repressing the spread of cancer and, in some instances, actually arresting some forms of cancer. Particular progress has been made in the development of anticancer drugs and techniques of delivering these drugs. There has also been significant progress in the discovery and development of antitumor agents which have proven effective in treating and repressing a variety of tumors including malignant and other rapidly growing tumors.

One family of antitumor agents which has proven effective in the treatment of some types of cancerous tumors and therefore has potential for use in cancer chemotherapy are actinomycins. Actinomycin was the first crystalline antibiotic derived from streptomyces. As early as 1952 it was demonstrated that actinomycins, actinomycin C in this case, had a remarkable effect in repressing the growth of tumors such as Hodgkins's disease and lymphomas, both in animals and in man. Subsequent studies throughout the world have indicated that actinomycins are very effective in inhibiting the growth of a variety of tumors. However, various preparations of actinomycins, including actinomycin D, have shown excessive toxicity to the host, which toxicity has been a most serious factor, preventing general use of these antibiotics in cancer chemotherapy. Toxicity of other potential cancer-fighting drugs in addition to actinomycins is a very serious drawback, as these drugs do exhibit a significant inhibiting effect on a variety of tumors. Consequently, it would be desirable to find a means of introducing these drugs to the body in a form in which the toxicity of the drug to the host is reduced.

Therefore, it is an object of the present invention to provide a chemotherapy method for various tumors.

It is another object of the present invention to provide a chemotherapy method for cancerous tumors.

Another object of the present invention is to provide means for introducing antitumor drugs in chemotherapy methods for cancerous tumors whereby toxicity of the antitumor drug to the host is reduced.

Another object of the present invention is to provide a method for reducing toxicity of antitumor drugs when introduced into the body for chemotherapy.

A particular object of the present invention is to provide a method for reducing the toxicity of actinomycins when introduced into the body for chemotherapy for cancerous tumors.

BRIEF DESCRIPTION OF THE DRAWINGS

Other objects and advantages of the present invention will become apparent upon reading the following description of the invention and with reference to the drawings in which:

FIG. 1 graphically illustrates the increased survival time of mice given a single treatment in accordance with the present invention.

FIG. 2 graphically illustrates the increased survival time of mice given multiple treatments in accordance with the present invention.

SUMMARY OF THE INVENTION

In accordance with the present invention, tumors are treated by a chemotherapy technique in which an antitumor drug is encapsulated within liposomes and the liposome-encapsulated antitumor drug is introduced into the body, whereby the encapsulated antitumor drug is delivered to and penetrates into the tumor cells, is slowly released, and induces degeneration and death of the tumor cells. Further in accordance with the present invention, toxicity of antitumor drugs which normally exhibit a toxicity to the host is reduced when the antitumor drug is introduced into the body in accordance with the technique described above.

In accordance with a specific embodiment of the present invention, liposome encapsulation of actinomycins, and actinomycin D in particular, has been found to be significantly effective in fighting tumor cells in the body while reducing the toxicity of the actinomycin to the host.

Other aspects of the present invention will be better understood and more appreciated upon reading the following detailed description of a specific embodiment of the present invention.

DETAILED DESCRIPTION OF THE INVENTION

In accordance with the present invention, antitumor drugs encapsulated within liposomes and inroduced into the body have been found to be effective in causing degeneration and death of tumor cells with a reduced toxicity to the host body. As a specific example, actinomycins, and actinomycin D in particular, have been encapsulated within liposomes and shown to be successful in increasing the survival time of mice treated in accordance with the present invention.

Actinomycin D or dactinomycin was selected for encapsulation within liposomes because although actinomycin is a known antineoplastic agent, widespread use in chemotherapy has been limited because it exhibits excessive toxicity. Actinomycin D is described more fully under the description of dactinomycin, page 319 of the Eighth Edition of the Merck Index, which description is incorporated herein by reference.

It was found that actinomycin D could be encapsulated in liposomes, which are small spherules composed of lipid layers separated by entrapped aqueous layers. Liposomes can be formed by drying a lipid mixture to form a thin film on the walls of a flask and introducing an aqueous solution into the flask to wet the thin film of the lipid on the walls. When the contents of the flask are then shaken, small spherules are formed which have encapsulated layers of the aqueous solution alternating with lipid layers. As an example, liposomes were prepared with a mixture of 3.0 mg of egg lecithin and 3.0 mg of cholesterol dissolved in chloroform. Actinomycin D was dissolved in 8 mM calcium chloride at a concentration of 0.5 mg in 1 ml. The aqueous actinomycin solution was slowly added to the dried film of lecithin-cholesterol mixture with immediate and constant stirring. The resulting liposomes consisted of aqueous layers containing the actinomycin D encapsulated between the lipid bilayers. Preparation of similar liposomes, and in particular those containing chelating agents EDTA and DTPA, is fully described in a previous article c-authored by the applicants entitled "Therapy of Intracellular Plutonium by Liposome-Encapsulated Chelating Agent", published in the April 20, 1973 issue of Science, incorporated herein by reference.

While the liposome-encapsulated actinomycin D referred to in the following examples was prepared in accordance with the just-described techniques, it should be understood that minor variations in the technique of liposome encapsulation of actinomycin D or other antitumor drugs is permissible. For example, liposomes have also been prepared with actinomycin D incorporated into the lipid phase and made with 8 mM calcium chloride solution. Also, the lipid composition of the liposomes can be varied by addition of different amounts of cholesterol or by addition of stearylamine or phosphatidylserine to impart positive or negative surface charge to the resulting liposome.

The incorporation of actinomycin D into the lipid phase of liposome was found to greatly increase the uptake in mouse tissue examined, particularly in lungs where an increase of six to eightfold was observed compared to liposomes with actinomycin D in the aqueous phase. However, the lipid-phase actinomycin D liposomes showed a much lower affinity for gut wall, where a decrease of about fivefold was found compared to the aqueous actinomycin D liposomes. The surface charge of liposomes was not found to have a significant effect on the tissue uptake and retention of liposomes containing EDTA. Liposomes of neutral surface charge with greater proportions of cholesterol were usually taken up and retained to a greater extent, probably because of the stabilizing effect of cholesterol upon the liposomal membranes rather than specific cell membrane interactions with the liposomes. However, by appropriate modification of the surface characteristics of liposomes, it may be possible to achieve selective delivery of drugs into the desired animal tissues.

The effectiveness of liposome-encapsulated antitumor drugs in combating body tumors and the successful reduction of toxicity of the antitumor drug to the host body by encapsulation within liposomes will be appreciated by considering the following examples wherein actinomycin D was encapsulated in liposomes in accordance with the above techniques. The liposomes containing the actinomycin D were resuspended in 8 mM calcium chloride for injection. The amount of actinomycin D encapsulated within liposomes was determined by tagging with a tritium-substituted actinomycin D, and similarly, the doses used for injection were calculated from subsequent analysis of the radioactivity contained in the liposomes.

Female CF No. 1 (Carworth Farms) mice, 3 months of age, weighing between 27 and 29 grams, were used in each instance in these experiments. For toxicity studies, groups of 15 or 20 mice were given actinomycin D at different levels, either in the nonencapsulated or in the liposome-encapsulated forms. Toxicity of actinomycin D was tested by both intravenous and intraperitoneal injection. Experiments were carried out to test the therapeutic efficacy of the encapsulated actinomycin D against Ehrlich ascites (E. A.) tumor cells in vivo. In Experiment I, mice recieved $20 \times 10^6$ E.A. cells by intraperitoneal injection. After 5 days, separate groups were treated with one of the following: (1) 0.4 ml of 8 mM calcium chloride, (2) nonencapsulated actinomycin D (0.75 mg/kg), or (3) liposome-encapsulated actinomycin D (0.75 mg/kg). In Experiment II, two groups of 10 mice were similarly inoculated. Treatment of one group was begun after 3 days with 0.5 mg/kg of encapsulated actinomycin D, followed by injection on 4 consecutive days with 0.25 mg/kg. All injections were given intraperitoneally, in a volume of 0.4 ml in Experiment I, 0.2 ml in Experiment II.

Electron microscopic studies of tissue cells were also conducted. For the electron microscopic studies, a mouse was inoculated with E.A. cells in the manner described above. Five days after the inoculation, liposomes containing actinomycin D at a concentration of 2 mg/kg were injected intraperitoneally. At intervals of 1, 6, 12 and 24 hours after the liposome injection, 0.2 ml of ascites fluid was aspirated from the mouse abdominal cavity with a syringe. The fluid was centrifuged and the pellet of E.A. cells was fixed and processed for examination in an electron microscope. Electron microscope observations showed rapid penetration of liposomes containing actinomycin D in E.A. cells. Light and electron microscopic examination of E.A. tumor cells was also carried out 1 hour to 5 days after treatment with liposome-encapsulated and nonencapsulated actinomycin D at a dose of 1 mg/kg. In each instance, liposomes were observed inside E.A. cells within an hour after injection. By 3 hours, and as early as 1 hour after liposomal actinomycin D injection in the first case, the E.A. cells displayed drastic morphological changes. The cells became round and exhibited fewer cytoplasmic extensions. There was an increase in lipid droplets, lyosomes and autophagic vacuoles and the ribosomes were clumped into distinct clusters. Fewer dividing cells were seen, at least after 24 hours post-treatment. The nuclei showed condensed chromatin with adjacent distinct ribosomelike clusters and in extremis became pyknotic. Significantly fewer E. A. cells were damaged in mice receiving nonencapsulated actinomycin D, the cytoplasmic changes also being less pronounced and extending only over a short period of time. Severe cellular damages as well as cell death were seen in samples examined at subsequent time intervals after injection.

Studies of the toxicity of the actinomycin showed that liposome encapsulation of actinomycin D drastically reduced the toxicity of the actinomycin to the host body. The $LD_{50}$ for actinomycin D given intravenously was $0.43 \pm 0.04$ mg/kg. At doses of 0.5 mg/kg and above, most of the deaths occurred within 24 hours. At lowest dose used, 0.3 mg/kg, the average survival time of the 8 decedents out of 20 injected was 3.5 days. After intraperitoneal injection, the $LD_{50}$ was $0.59 \pm 0.17$ mg/kg, with some of the decedents surviving as long as 14 days. In contrast, no deaths were observed in mice given liposome-encapsulated actinomycin D after either intravenous injection at 1 mg/kg or intraperitoneal injection at 2 mg/kg.

Chemotherapy studies were also conducted to demonstrate the effect of the treatment with liposome-encapsulated actinomycin D on the survival time of mice bearing E.A. tumors. These effects are clearly illustrated in the drawings.

Referring to FIG. 1, there is illustrated the therapeutic effect of liposome-encapsulated actinomycin D on the survival of mice bearing E.A. tumor following single treatments given at 5 days after inoculation of $20 \times 10^6$ E.A. cells. A control is represented by line 11 on the graph, liposome-encapsulated actinomycin D at 0.75 mg/kg represented by line 12 and nonencapsulated actinomycin D at 0.75 mg/kg represented by line 13. As can be seen, after a single injection, the survival time of mice receiving the encapsulated drug increased from the control average of 7.4 ± 3.11 days to 13.2 ± 3.19 days after treatment. The survival time of mice receiving nonencapsulated actinomycin D was slightly, but not significantly, less than the controls.

Referring to FIG. 2, there is shown graphically the therapeutic effect of liposome-encapsulated actinomycin D on the survival of mice bearing E.A. tumor with multiple daily treatments starting at day 3 after inoculation with $20 \times 10^6$ E.A. cells. In FIG. 2, the control is represented by line 14, liposome-encapsulated actinomycin D, first dose 0.50 mg/kg followed by four consecutive injections of 0.25 mg/kg, is represented by line 15. As is readily apparent from the graph, the increase in survival time after mutliple injections of encapsulated actinomycin D was even more impressive: 7.3 ±2.26 days for the control versus 17.6 ± 2.17 days for the encapsulated actinomycin D. All of the control animals died before the first death occurred in the treatment group. In a separate experiment, it was observed that injection of liposomes prepared with KCl instead of actinomycin D had no effect on survival time.

It is apparent, then, from the toxicity, chemotherapy and electron microscope studies, that actinomycin D encapsulated within liposomes is remarkably less toxic than the nonencapsulated form; liposome-encapsulated actinomycin at an actinomycin dose normally toxic to mice prolongs the mean survival time of mice bearing E.A. tumor; and liposomes containing actinomycin D penetrate the tumor cells, transporting the drug into the tumors wherein the drug induces cell death.

While the invention has been described in terms of a specific embodiment and with use of actinomycin D, it should be understood that the invention is not so limited but is equally applicable to other antitumor drugs and, in fact, other antitumor drugs have been shown to be successfuly encapsulated within liposomes. For example, among those antitumor drugs which have been successfully encapsulated within liposomes are daunomycin, adriamycin, mustargen, mitomycin C, cytarabine, puromycin, and cycloheximide. Since it is believed that other antitumor drugs can likewise be encapsulated, the invention should not be limited to the specific examples listed but should be construed in its broader aspects in accordance with the appended claims.

The embodiments of the invention in which an exclusive property or privilege is claimed are defined as follows:

1. A method of reducing the toxicity of actinomycin D when employed as an antineoplastic agent in an animal or man which comprises administering to said animal or man an effective antineoplastic amount of liposome encapsulated actinomycin D.

2. The method of claim 1 wherein said liposome encapsulated actinomycin D is contained within aqueous solution layers entrapped between lipid bilayers.

3. The method in accordance with claim 1 wherein said actinomycin D is encapsulated within liposomes by: dissolving a mixture of lecithin and cholesterol in chloroform; dissolving the actinomycin D in $CaCl_2$ solution; forming a dried film of the lecithin-cholesterol mixture; and adding the actinomycin D-$CaCl_2$ solution to the dried film so as to form the liposomes encapsulating the actinomycin D.

4. The method of claim 1 wherein said liposome encapsulated actinomycin D is administered by intravenous or intraperitoneal injection.

* * * * *